(12) United States Patent
Kröll

(10) Patent No.: US 11,630,171 B2
(45) Date of Patent: Apr. 18, 2023

(54) METHOD AND MAGNETIC RESONANCE APPARATUS FOR AUTOMATIC INTERACTION WITH A PATIENT

(71) Applicant: Siemens Healthcare GmbH, Erlangen (DE)

(72) Inventor: Maria Kröll, Erlangen (DE)

(73) Assignee: Siemens Healthcare GmbH, Erlangen (DE)

( * ) Notice: Subject to any disclaimer, the term of this patent is extended or adjusted under 35 U.S.C. 154(b) by 0 days.

(21) Appl. No.: 17/530,663

(22) Filed: Nov. 19, 2021

(65) Prior Publication Data

US 2022/0171003 A1 Jun. 2, 2022

(30) Foreign Application Priority Data

Nov. 30, 2020 (DE) .................. 10 2020 215 064.8

(51) Int. Cl.
| | |
|---|---|
| *G01R 33/28* | (2006.01) |
| *A61B 5/055* | (2006.01) |
| *G10L 15/22* | (2006.01) |
| *G01R 33/54* | (2006.01) |

(52) U.S. Cl.
CPC ............ *G01R 33/283* (2013.01); *A61B 5/055* (2013.01); *G01R 33/288* (2013.01); *G01R 33/543* (2013.01); *G10L 15/22* (2013.01); *G10L 2015/225* (2013.01)

(58) Field of Classification Search
None
See application file for complete search history.

(56) References Cited

U.S. PATENT DOCUMENTS

| | | | |
|---|---|---|---|
| 11,327,128 B2 * | 5/2022 | Weiss ................... | G01R 33/288 |
| 2013/0342350 A1 * | 12/2013 | Popescu ................ | G08B 21/02 |
| | | | 340/573.1 |
| 2015/0045654 A1 | 2/2015 | Lee et al. | |
| 2015/0253979 A1 | 9/2015 | Popescu | |
| 2019/0125306 A1 * | 5/2019 | Oh .......................... | G16H 40/63 |

(Continued)

FOREIGN PATENT DOCUMENTS

DE 102014204251 A1 9/2015

OTHER PUBLICATIONS

German Office Action dated Sep. 16, 2021.

*Primary Examiner* — Rodney E Fuller
(74) *Attorney, Agent, or Firm* — Harness, Dickey & Pierce, P.L.C.

(57) ABSTRACT

A method is for automatic interaction with a patient during a magnetic resonance examination with a magnetic resonance apparatus. In an embodiment, the method includes detecting an acoustic utterance of the patient; processing the acoustic utterance of the patient via a speech processor, the processing of the acoustic utterance including at least determining the communication as a function of the acoustic utterance and checking the communication for a correlation with a parameter of the magnetic resonance examination; determining the output as a function of the communication of the patient and the parameter of the magnetic resonance examination and providing the output. A magnetic resonance apparatus of an embodiment includes at least a processor to carry out an embodiment of the method. The method can further be stored on a computer program product or medium for execution by a processor.

23 Claims, 4 Drawing Sheets

(56) References Cited

U.S. PATENT DOCUMENTS

2020/0020334 A1\* 1/2020 Kang ................ G10L 15/22
2020/0143809 A1\* 5/2020 Lee .................. G06F 3/167
2020/0243090 A1\* 7/2020 Schneider .......... A61B 5/055

\* cited by examiner

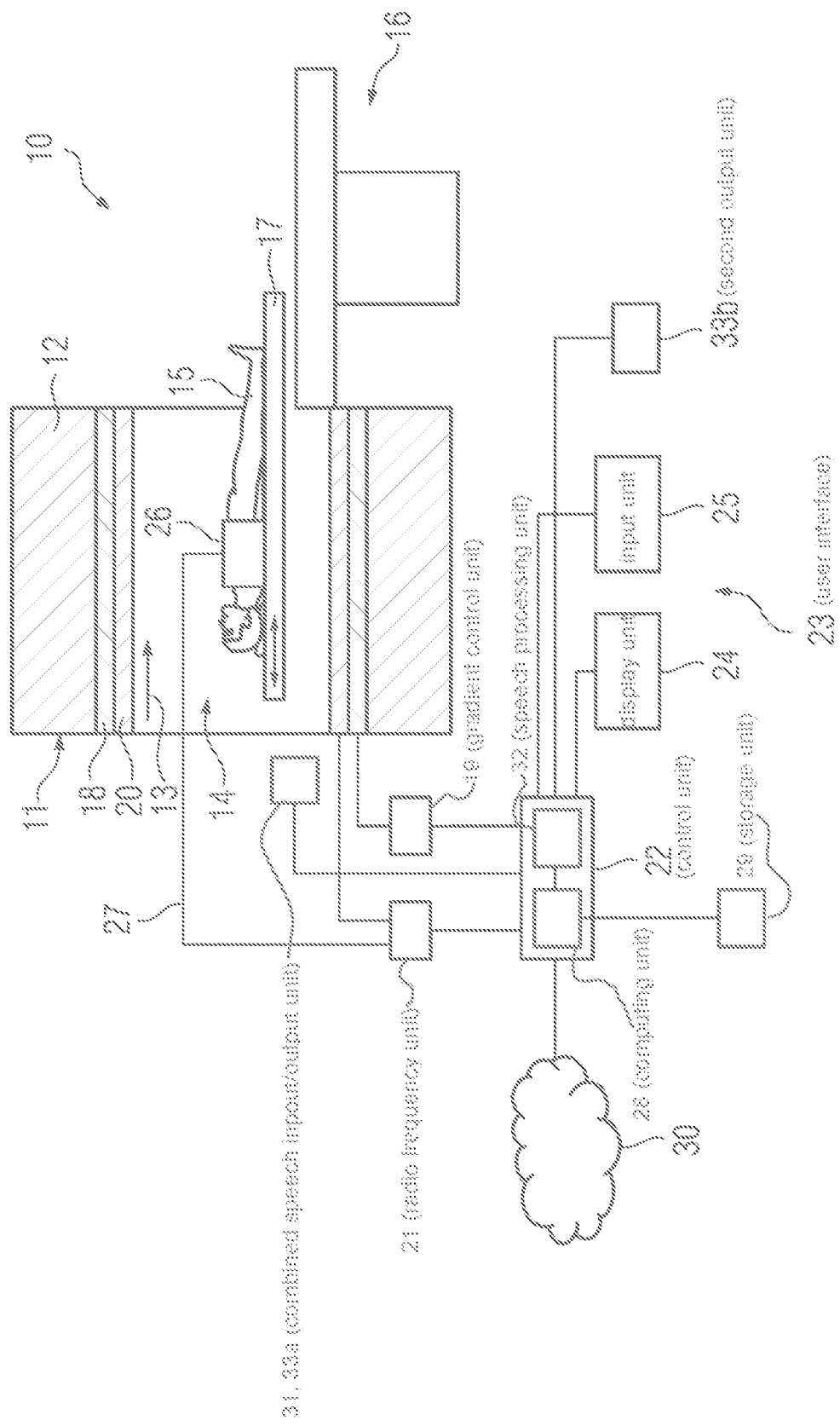

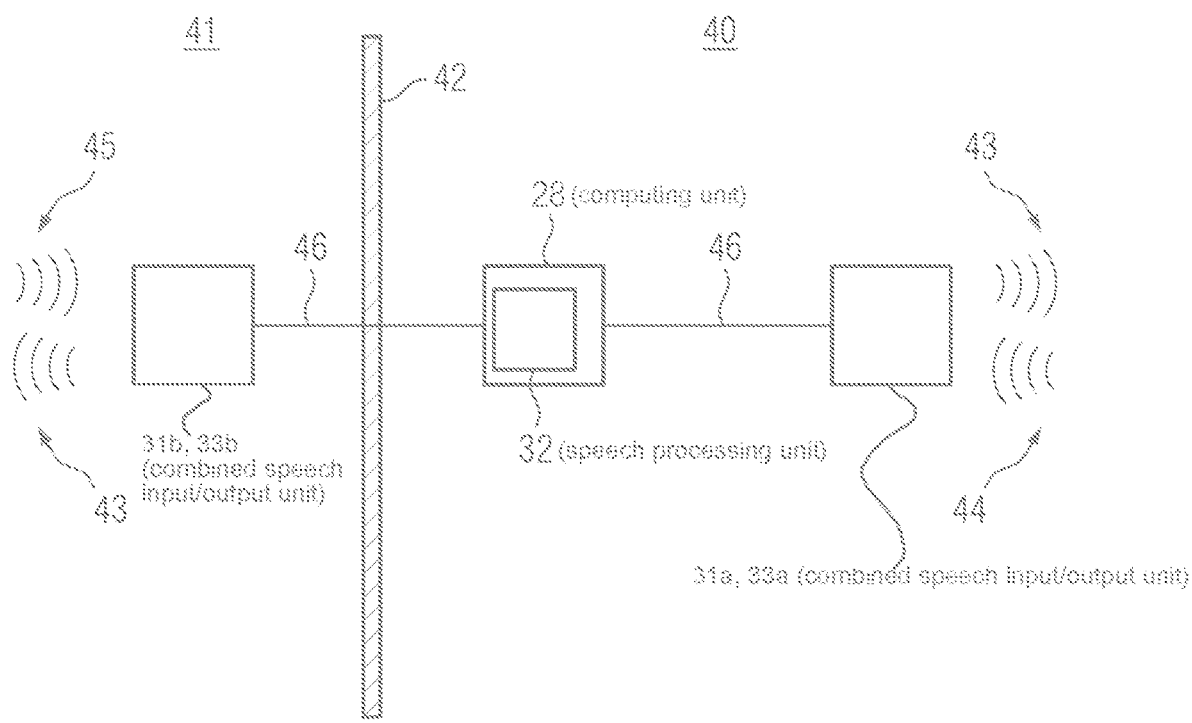

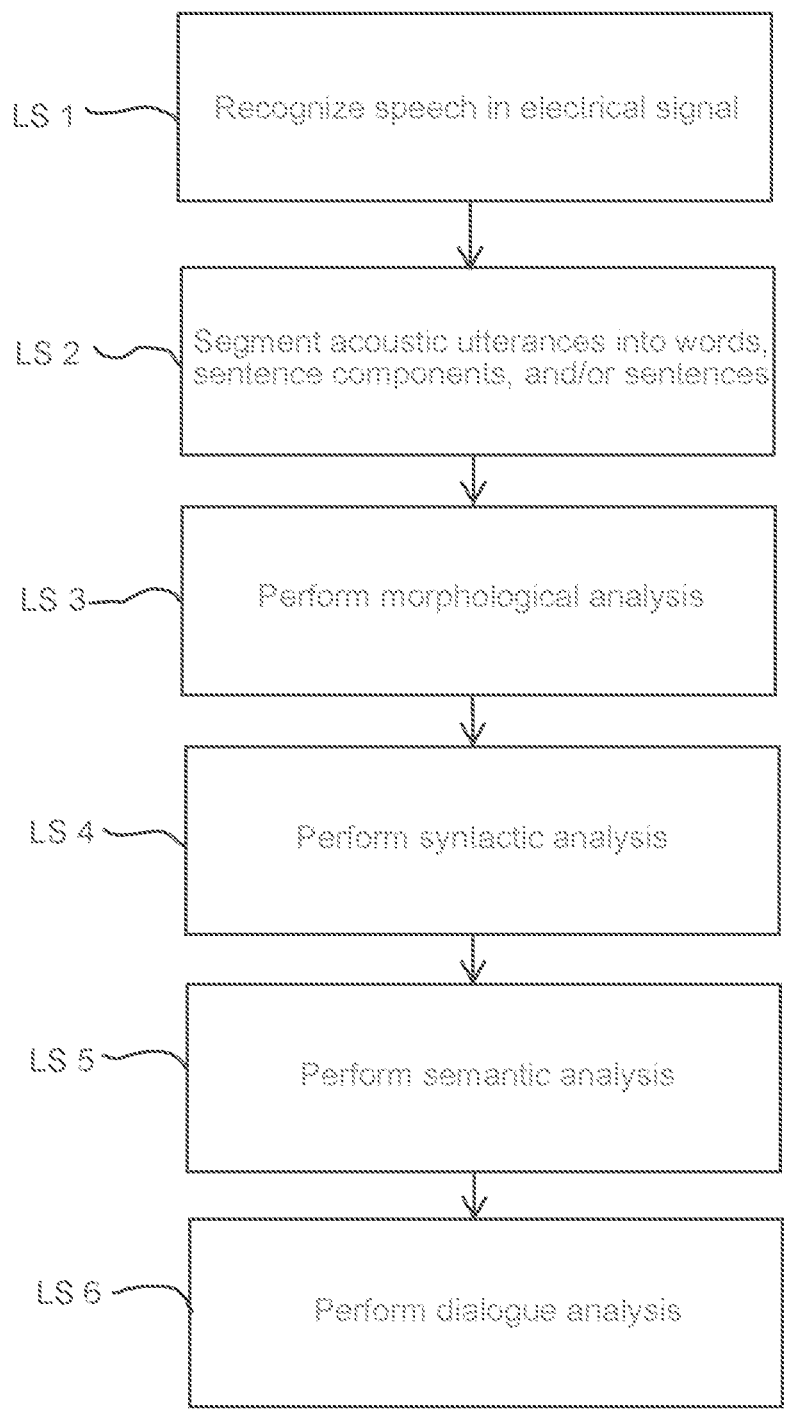

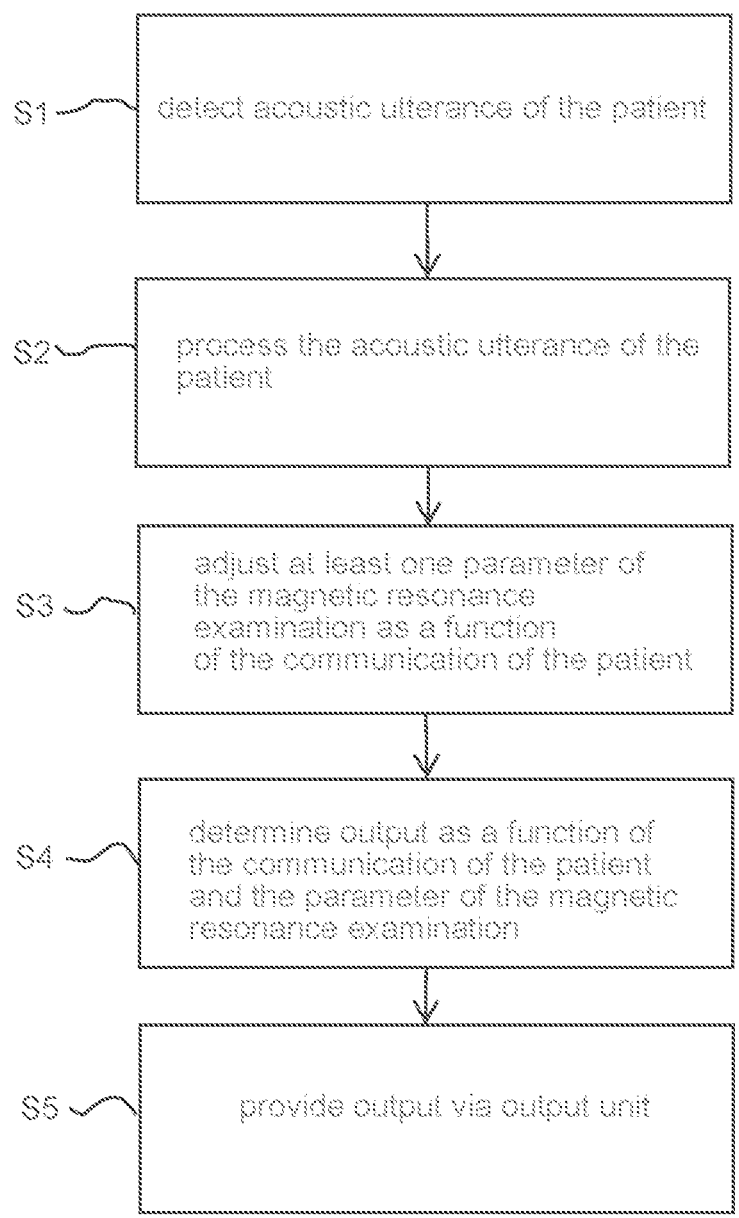

METHOD AND MAGNETIC RESONANCE APPARATUS FOR AUTOMATIC INTERACTION WITH A PATIENT

PRIORITY STATEMENT

The present application hereby claims priority under 35 U.S.C. § 119 to German patent application number DE 102020215064.8 filed Nov. 30, 2020, the entire contents of which are hereby incorporated herein by reference.

FIELD

Example embodiments of the invention generally relate to a method for automatic interaction with a patient during a magnetic resonance examination, wherein the automatic interaction comprises at least providing an output as a function of a communication of the patient; and to a magnetic resonance apparatus with a computing unit for carrying out an inventive method; and to a computer program product, which can be loaded directly into a data storage unit of a computing unit of an inventive magnetic resonance apparatus.

BACKGROUND

During a magnetic resonance examination, a patient is conventionally positioned inside an imaging region of a magnetic resonance apparatus and thus cut off from their surroundings. The situation can occur where the patient wishes to communicate with a user of the magnetic resonance apparatus but does not have the courage to express themselves. If the patient does express themselves, the user is typically distracted from current tasks, such as setting imaging parameters and/or preparing a magnetic resonance measurement of a subsequent patient. Such interruptions can result in errors when carrying out the magnetic resonance examination and preparing subsequent magnetic resonance examinations and impair the quality of generated magnetic resonance image data.

Similarly, the situation can occur where members of the medical staff are occupied by additional tasks and will not be attentive to the communication of the patient. Listening to a patient's concern can reassure the patient, however, and thus contribute to a smooth implementation of the magnetic resonance examination and a high quality of the generated magnetic resonance image data.

Communication between patient and members of the medical staff can currently be achieved via an intercom. This kind of communication assumes that both the patient and the user are actively participating in the communication. In particular, the user typically has to interrupt their activity as soon as the patient begins communication.

SUMMARY

At least one embodiment of the invention reduces or avoids interruptions to an activity of the medical staff due to a communication with the patient. At least one embodiment of the invention reacts to a communication of the patient to enable a smooth progression of the magnetic resonance examination.

Advantageous embodiments and expedient developments are the subject matter of the claims.

At least one embodiment of the inventive method enables automatic interaction with a patient during a magnetic resonance examination with a magnetic resonance apparatus, wherein the automatic interaction comprises at least providing an output as a function of a communication of the patient. The inventive method comprises:

detecting an acoustic utterance of the patient via a speech input unit,
 processing the acoustic utterance of the patient via a speech processing unit, wherein processing of the acoustic utterance comprises at least
  determining the communication as a function of the acoustic utterance and
  checking the communication for a correlation with a parameter of the magnetic resonance examination,
 determining the output as a function of the communication of the patient and the parameter of the magnetic resonance examination and
 providing the output via an output unit.

At least one embodiment is directed to a magnetic resonance apparatus comprising a computing unit, a speech input unit, a speech processing unit and an output unit, wherein the computing unit is designed to coordinate a method of at least one embodiment of the invention and carry it out via the magnetic resonance apparatus.

At least one embodiment of the invention is directed to a computer program product which can be loaded into a data storage unit of a computing unit of the magnetic resonance apparatus and which has program code segments to carry out at least one embodiment of an inventive method when the computer program product is run in the computing unit of the magnetic resonance apparatus.

In at least one embodiment, the computer program product is stored, for example, on a computer-readable medium or on a network, a server or a Cloud, from where it can be loaded into the processor of a local computing unit. The computing unit can be designed as a stand-alone system component or as part of the magnetic resonance apparatus. Furthermore, control information of the computer program product can be stored on an electronically readable data carrier. The control information of the electronically readable data carrier can be configured in such a way that it carries out at least one embodiment of an inventive method when the data carrier is used in the computing unit of the magnetic resonance apparatus. Examples of electronically readable data carriers are a DVD, a magnetic tape, a USB stick or any other data storage unit on which electronically readable control information, in particular software, is stored. When this control information is read from the data carrier and transferred to a control unit and/or the computing unit of the magnetic resonance apparatus, all inventive embodiments of the described, inventive method can be carried out.

In at least one embodiment, a method is for automatic interaction with a patient during a magnetic resonance examination with a magnetic resonance apparatus, comprising:

detecting an acoustic utterance of the patient;
 processing the acoustic utterance of the patient via a speech processor, the processing of the acoustic utterance comprising at least
  determining a communication of the patient as a function of the acoustic utterance, and
  checking the communication for a correlation with a parameter of the magnetic resonance examination;
 determining an output as a function of the communication of the patient and the parameter of the magnetic resonance examination; and providing the output.

In at least one embodiment, a magnetic resonance apparatus comprises:
- a computing device;
- a speech input device;
- a speech processor; and
- an output device, the computing device being designed to
  - detect an acoustic utterance of the patient via the speech input device;
  - process the acoustic utterance of the patient via a speech processor, processing of the acoustic utterance comprising at least
    - determine a communication of the patient as a function of the acoustic utterance, and
    - check the communication for a correlation with a parameter of the magnetic resonance examination;
  - determine an output as a function of the communication of the patient and the parameter of the magnetic resonance examination; and
  - provide the output via the output device.

In at least one embodiment, a non-transitory computer program product is directly loadable into a data storage of a computing device of a magnetic resonance apparatus, including program code segments to carry out the method of an embodiment when the computer program product is run in the computing device of the magnetic resonance apparatus.

In at least one embodiment, a non-transitory computer readable medium stores a computer program including program code segments, to carry out the method of an embodiment when the computer program is run by a computing device of a magnetic resonance apparatus.

BRIEF DESCRIPTION OF THE DRAWINGS

Further advantages and details of the present invention can be found in the example embodiments described below and with reference to the drawings, in which:

FIG. 1 shows a schematic representation of an embodiment of an inventive magnetic resonance apparatus, FIG. 2 shows an example arrangement of a speech input unit, a speech processing unit and an output unit of an embodiment of an inventive magnetic resonance apparatus, FIG. 3 shows an example flowchart of processing of an acoustic utterance according to one embodiment of an inventive method, FIG. 4 shows a flowchart of one embodiment of an inventive method.

DETAILED DESCRIPTION OF THE EXAMPLE EMBODIMENTS

The drawings are to be regarded as being schematic representations and elements illustrated in the drawings are not necessarily shown to scale. Rather, the various elements are represented such that their function and general purpose become apparent to a person skilled in the art. Any connection or coupling between functional blocks, devices, components, or other physical or functional units shown in the drawings or described herein may also be implemented by an indirect connection or coupling. A coupling between components may also be established over a wireless connection. Functional blocks may be implemented in hardware, firmware, software, or a combination thereof.

Various example embodiments will now be described more fully with reference to the accompanying drawings in which only some example embodiments are shown. Specific structural and functional details disclosed herein are merely representative for purposes of describing example embodiments. Example embodiments, however, may be embodied in various different forms, and should not be construed as being limited to only the illustrated embodiments. Rather, the illustrated embodiments are provided as examples so that this disclosure will be thorough and complete, and will fully convey the concepts of this disclosure to those skilled in the art. Accordingly, known processes, elements, and techniques, may not be described with respect to some example embodiments. Unless otherwise noted, like reference characters denote like elements throughout the attached drawings and written description, and thus descriptions will not be repeated. At least one embodiment of the present invention, however, may be embodied in many alternate forms and should not be construed as limited to only the example embodiments set forth herein.

It will be understood that, although the terms first, second, etc. may be used herein to describe various elements, components, regions, layers, and/or sections, these elements, components, regions, layers, and/or sections, should not be limited by these terms. These terms are only used to distinguish one element from another. For example, a first element could be termed a second element, and, similarly, a second element could be termed a first element, without departing from the scope of example embodiments of the present invention. As used herein, the term "and/or," includes any and all combinations of one or more of the associated listed items. The phrase "at least one of" has the same meaning as "and/or".

Spatially relative terms, such as "beneath," "below," "lower," "under," "above," "upper," and the like, may be used herein for ease of description to describe one element or feature's relationship to another element(s) or feature(s) as illustrated in the figures. It will be understood that the spatially relative terms are intended to encompass different orientations of the device in use or operation in addition to the orientation depicted in the figures. For example, if the device in the figures is turned over, elements described as "below," "beneath," or "under," other elements or features would then be oriented "above" the other elements or features. Thus, the example terms "below" and "under" may encompass both an orientation of above and below. The device may be otherwise oriented (rotated 90 degrees or at other orientations) and the spatially relative descriptors used herein interpreted accordingly. In addition, when an element is referred to as being "between" two elements, the element may be the only element between the two elements, or one or more other intervening elements may be present.

Spatial and functional relationships between elements (for example, between modules) are described using various terms, including "connected," "engaged," "interfaced," and "coupled." Unless explicitly described as being "direct," when a relationship between first and second elements is described in the above disclosure, that relationship encompasses a direct relationship where no other intervening elements are present between the first and second elements, and also an indirect relationship where one or more intervening elements are present (either spatially or functionally) between the first and second elements. In contrast, when an element is referred to as being "directly" connected, engaged, interfaced, or coupled to another element, there are no intervening elements present. Other words used to describe the relationship between elements should be interpreted in a like fashion (e.g., "between," versus "directly between," "adjacent," versus "directly adjacent," etc.).

The terminology used herein is for the purpose of describing particular embodiments only and is not intended to be limiting of example embodiments of the invention. As used herein, the singular forms "a," "an," and "the," are intended to include the plural forms as well, unless the context clearly indicates otherwise. As used herein, the terms "and/or" and "at least one of" include any and all combinations of one or more of the associated listed items. It will be further understood that the terms "comprises," "comprising," "includes," and/or "including," when used herein, specify the presence of stated features, integers, steps, operations, elements, and/or components, but do not preclude the presence or addition of one or more other features, integers, steps, operations, elements, components, and/or groups thereof. As used herein, the term "and/or" includes any and all combinations of one or more of the associated listed items. Expressions such as "at least one of," when preceding a list of elements, modify the entire list of elements and do not modify the individual elements of the list. Also, the term "example" is intended to refer to an example or illustration.

When an element is referred to as being "on," "connected to," "coupled to," or "adjacent to," another element, the element may be directly on, connected to, coupled to, or adjacent to, the other element, or one or more other intervening elements may be present. In contrast, when an element is referred to as being "directly on," "directly connected to," "directly coupled to," or "immediately adjacent to," another element there are no intervening elements present.

It should also be noted that in some alternative implementations, the functions/acts noted may occur out of the order noted in the figures. For example, two figures shown in succession may in fact be executed substantially concurrently or may sometimes be executed in the reverse order, depending upon the functionality/acts involved.

Unless otherwise defined, all terms (including technical and scientific terms) used herein have the same meaning as commonly understood by one of ordinary skill in the art to which example embodiments belong. It will be further understood that terms, e.g., those defined in commonly used dictionaries, should be interpreted as having a meaning that is consistent with their meaning in the context of the relevant art and will not be interpreted in an idealized or overly formal sense unless expressly so defined herein.

Before discussing example embodiments in more detail, it is noted that some example embodiments may be described with reference to acts and symbolic representations of operations (e.g., in the form of flow charts, flow diagrams, data flow diagrams, structure diagrams, block diagrams, etc.) that may be implemented in conjunction with units and/or devices discussed in more detail below. Although discussed in a particularly manner, a function or operation specified in a specific block may be performed differently from the flow specified in a flowchart, flow diagram, etc. For example, functions or operations illustrated as being performed serially in two consecutive blocks may actually be performed simultaneously, or in some cases be performed in reverse order. Although the flowcharts describe the operations as sequential processes, many of the operations may be performed in parallel, concurrently or simultaneously. In addition, the order of operations may be re-arranged. The processes may be terminated when their operations are completed, but may also have additional steps not included in the figure. The processes may correspond to methods, functions, procedures, subroutines, subprograms, etc.

Specific structural and functional details disclosed herein are merely representative for purposes of describing example embodiments of the present invention. This invention may, however, be embodied in many alternate forms and should not be construed as limited to only the embodiments set forth herein.

Units and/or devices according to one or more example embodiments may be implemented using hardware, software, and/or a combination thereof. For example, hardware devices may be implemented using processing circuitry such as, but not limited to, a processor, Central Processing Unit (CPU), a controller, an arithmetic logic unit (ALU), a digital signal processor, a microcomputer, a field programmable gate array (FPGA), a System-on-Chip (SoC), a programmable logic unit, a microprocessor, or any other device capable of responding to and executing instructions in a defined manner. Portions of the example embodiments and corresponding detailed description may be presented in terms of software, or algorithms and symbolic representations of operation on data bits within a computer memory. These descriptions and representations are the ones by which those of ordinary skill in the art effectively convey the substance of their work to others of ordinary skill in the art. An algorithm, as the term is used here, and as it is used generally, is conceived to be a self-consistent sequence of steps leading to a desired result. The steps are those requiring physical manipulations of physical quantities. Usually, though not necessarily, these quantities take the form of optical, electrical, or magnetic signals capable of being stored, transferred, combined, compared, and otherwise manipulated. It has proven convenient at times, principally for reasons of common usage, to refer to these signals as bits, values, elements, symbols, characters, terms, numbers, or the like.

It should be borne in mind, however, that all of these and similar terms are to be associated with the appropriate physical quantities and are merely convenient labels applied to these quantities. Unless specifically stated otherwise, or as is apparent from the discussion, terms such as "processing" or "computing" or "calculating" or "determining" of "displaying" or the like, refer to the action and processes of a computer system, or similar electronic computing device/hardware, that manipulates and transforms data represented as physical, electronic quantities within the computer system's registers and memories into other data similarly represented as physical quantities within the computer system memories or registers or other such information storage, transmission or display devices.

In this application, including the definitions below, the term 'module' or the term 'controller' may be replaced with the term 'circuit.' The term 'module' may refer to, be part of, or include processor hardware (shared, dedicated, or group) that executes code and memory hardware (shared, dedicated, or group) that stores code executed by the processor hardware.

The module may include one or more interface circuits. In some examples, the interface circuits may include wired or wireless interfaces that are connected to a local area network (LAN), the Internet, a wide area network (WAN), or combinations thereof. The functionality of any given module of the present disclosure may be distributed among multiple modules that are connected via interface circuits. For example, multiple modules may allow load balancing. In a further example, a server (also known as remote, or cloud) module may accomplish some functionality on behalf of a client module.

Software may include a computer program, program code, instructions, or some combination thereof, for independently or collectively instructing or configuring a hardware device to operate as desired. The computer program and/or program code may include program or computer-readable instructions, software components, software modules, data files, data structures, and/or the like, capable of being implemented by one or more hardware devices, such as one or more of the hardware devices mentioned above. Examples of program code include both machine code produced by a compiler and higher level program code that is executed using an interpreter.

For example, when a hardware device is a computer processing device (e.g., a processor, Central Processing Unit (CPU), a controller, an arithmetic logic unit (ALU), a digital signal processor, a microcomputer, a microprocessor, etc.), the computer processing device may be configured to carry out program code by performing arithmetical, logical, and input/output operations, according to the program code. Once the program code is loaded into a computer processing device, the computer processing device may be programmed to perform the program code, thereby transforming the computer processing device into a special purpose computer processing device. In a more specific example, when the program code is loaded into a processor, the processor becomes programmed to perform the program code and operations corresponding thereto, thereby transforming the processor into a special purpose processor.

Software and/or data may be embodied permanently or temporarily in any type of machine, component, physical or virtual equipment, or computer storage medium or device, capable of providing instructions or data to, or being interpreted by, a hardware device. The software also may be distributed over network coupled computer systems so that the software is stored and executed in a distributed fashion. In particular, for example, software and data may be stored by one or more computer readable recording mediums, including the tangible or non-transitory computer-readable storage media discussed herein.

Even further, any of the disclosed methods may be embodied in the form of a program or software. The program or software may be stored on a non-transitory computer readable medium and is adapted to perform any one of the aforementioned methods when run on a computer device (a device including a processor). Thus, the non-transitory, tangible computer readable medium, is adapted to store information and is adapted to interact with a data processing facility or computer device to execute the program of any of the above mentioned embodiments and/or to perform the method of any of the above mentioned embodiments.

Example embodiments may be described with reference to acts and symbolic representations of operations (e.g., in the form of flow charts, flow diagrams, data flow diagrams, structure diagrams, block diagrams, etc.) that may be implemented in conjunction with units and/or devices discussed in more detail below. Although discussed in a particularly manner, a function or operation specified in a specific block may be performed differently from the flow specified in a flowchart, flow diagram, etc. For example, functions or operations illustrated as being performed serially in two consecutive blocks may actually be performed simultaneously, or in some cases be performed in reverse order.

According to one or more example embodiments, computer processing devices may be described as including various functional units that perform various operations and/or functions to increase the clarity of the description. However, computer processing devices are not intended to be limited to these functional units. For example, in one or more example embodiments, the various operations and/or functions of the functional units may be performed by other ones of the functional units. Further, the computer processing devices may perform the operations and/or functions of the various functional units without sub-dividing the operations and/or functions of the computer processing units into these various functional units.

Units and/or devices according to one or more example embodiments may also include one or more storage devices. The one or more storage devices may be tangible or non-transitory computer-readable storage media, such as random access memory (RAM), read only memory (ROM), a permanent mass storage device (such as a disk drive), solid state (e.g., NAND flash) device, and/or any other like data storage mechanism capable of storing and recording data. The one or more storage devices may be configured to store computer programs, program code, instructions, or some combination thereof, for one or more operating systems and/or for implementing the example embodiments described herein. The computer programs, program code, instructions, or some combination thereof, may also be loaded from a separate computer readable storage medium into the one or more storage devices and/or one or more computer processing devices using a drive mechanism. Such separate computer readable storage medium may include a Universal Serial Bus (USB) flash drive, a memory stick, a Blu-ray/DVD/CD-ROM drive, a memory card, and/or other like computer readable storage media. The computer programs, program code, instructions, or some combination thereof, may be loaded into the one or more storage devices and/or the one or more computer processing devices from a remote data storage device via a network interface, rather than via a local computer readable storage medium. Additionally, the computer programs, program code, instructions, or some combination thereof, may be loaded into the one or more storage devices and/or the one or more processors from a remote computing system that is configured to transfer and/or distribute the computer programs, program code, instructions, or some combination thereof, over a network. The remote computing system may transfer and/or distribute the computer programs, program code, instructions, or some combination thereof, via a wired interface, an air interface, and/or any other like medium.

The one or more hardware devices, the one or more storage devices, and/or the computer programs, program code, instructions, or some combination thereof, may be specially designed and constructed for the purposes of the example embodiments, or they may be known devices that are altered and/or modified for the purposes of example embodiments.

A hardware device, such as a computer processing device, may run an operating system (OS) and one or more software applications that run on the OS. The computer processing device also may access, store, manipulate, process, and create data in response to execution of the software. For simplicity, one or more example embodiments may be exemplified as a computer processing device or processor; however, one skilled in the art will appreciate that a hardware device may include multiple processing elements or processors and multiple types of processing elements or processors. For example, a hardware device may include multiple processors or a processor and a controller. In addition, other processing configurations are possible, such as parallel processors.

The computer programs include processor-executable instructions that are stored on at least one non-transitory computer-readable medium (memory). The computer programs may also include or rely on stored data. The computer programs may encompass a basic input/output system (BIOS) that interacts with hardware of the special purpose computer, device drivers that interact with particular devices of the special purpose computer, one or more operating systems, user applications, background services, background applications, etc. As such, the one or more processors may be configured to execute the processor executable instructions.

The computer programs may include: (i) descriptive text to be parsed, such as HTML (hypertext markup language) or XML (extensible markup language), (ii) assembly code, (iii) object code generated from source code by a compiler, (iv) source code for execution by an interpreter, (v) source code for compilation and execution by a just-in-time compiler, etc. As examples only, source code may be written using syntax from languages including C, C++, C#, Objective-C, Haskell, Go, SQL, R, Lisp, Java®, Fortran, Perl, Pascal, Curl, OCaml, Javascript®, HTML5, Ada, ASP (active server pages), PHP, Scala, Eiffel, Smalltalk, Erlang, Ruby, Flash®, Visual Basic®, Lua, and Python®.

Further, at least one embodiment of the invention relates to the non-transitory computer-readable storage medium including electronically readable control information (processor executable instructions) stored thereon, configured in such that when the storage medium is used in a controller of a device, at least one embodiment of the method may be carried out.

The computer readable medium or storage medium may be a built-in medium installed inside a computer device main body or a removable medium arranged so that it can be separated from the computer device main body. The term computer-readable medium, as used herein, does not encompass transitory electrical or electromagnetic signals propagating through a medium (such as on a carrier wave); the term computer-readable medium is therefore considered tangible and non-transitory. Non-limiting examples of the non-transitory computer-readable medium include, but are not limited to, rewriteable non-volatile memory devices (including, for example flash memory devices, erasable programmable read-only memory devices, or a mask read-only memory devices); volatile memory devices (including, for example static random access memory devices or a dynamic random access memory devices); magnetic storage media (including, for example an analog or digital magnetic tape or a hard disk drive); and optical storage media (including, for example a CD, a DVD, or a Blu-ray Disc). Examples of the media with a built-in rewriteable non-volatile memory, include but are not limited to memory cards; and media with a built-in ROM, including but not limited to ROM cassettes; etc. Furthermore, various information regarding stored images, for example, property information, may be stored in any other form, or it may be provided in other ways.

The term code, as used above, may include software, firmware, and/or microcode, and may refer to programs, routines, functions, classes, data structures, and/or objects. Shared processor hardware encompasses a single microprocessor that executes some or all code from multiple modules. Group processor hardware encompasses a microprocessor that, in combination with additional microprocessors, executes some or all code from one or more modules. References to multiple microprocessors encompass multiple microprocessors on discrete dies, multiple microprocessors on a single die, multiple cores of a single microprocessor, multiple threads of a single microprocessor, or a combination of the above.

Shared memory hardware encompasses a single memory device that stores some or all code from multiple modules. Group memory hardware encompasses a memory device that, in combination with other memory devices, stores some or all code from one or more modules.

The term memory hardware is a subset of the term computer-readable medium. The term computer-readable medium, as used herein, does not encompass transitory electrical or electromagnetic signals propagating through a medium (such as on a carrier wave); the term computer-readable medium is therefore considered tangible and non-transitory. Non-limiting examples of the non-transitory computer-readable medium include, but are not limited to, rewriteable non-volatile memory devices (including, for example flash memory devices, erasable programmable read-only memory devices, or a mask read-only memory devices); volatile memory devices (including, for example static random access memory devices or a dynamic random access memory devices); magnetic storage media (including, for example an analog or digital magnetic tape or a hard disk drive); and optical storage media (including, for example a CD, a DVD, or a Blu-ray Disc). Examples of the media with a built-in rewriteable non-volatile memory, include but are not limited to memory cards; and media with a built-in ROM, including but not limited to ROM cassettes; etc. Furthermore, various information regarding stored images, for example, property information, may be stored in any other form, or it may be provided in other ways.

The apparatuses and methods described in this application may be partially or fully implemented by a special purpose computer created by configuring a general purpose computer to execute one or more particular functions embodied in computer programs. The functional blocks and flowchart elements described above serve as software specifications, which can be translated into the computer programs by the routine work of a skilled technician or programmer.

Although described with reference to specific examples and drawings, modifications, additions and substitutions of example embodiments may be variously made according to the description by those of ordinary skill in the art. For example, the described techniques may be performed in an order different with that of the methods described, and/or components such as the described system, architecture, devices, circuit, and the like, may be connected or combined to be different from the above-described methods, or results may be appropriately achieved by other components or equivalents.

At least one embodiment of the inventive method enables automatic interaction with a patient during a magnetic resonance examination with a magnetic resonance apparatus, wherein the automatic interaction comprises at least providing an output as a function of a communication of the patient. The inventive method comprises:
  detecting an acoustic utterance of the patient via a speech input unit,
  processing the acoustic utterance of the patient via a speech processing unit, wherein processing of the acoustic utterance comprises at least
    determining the communication as a function of the acoustic utterance and
    checking the communication for a correlation with a parameter of the magnetic resonance examination,
  determining the output as a function of the communication of the patient and the parameter of the magnetic resonance examination and
  providing the output via an output unit.

An interaction with a patient preferably comprises, in at least one embodiment, a communication and/or a dialogue with the patient. The communication can comprise, for example, a use of acoustic sounds and/or of speech. It is likewise conceivable, however, that the automatic interaction with the patient comprises visual and/or tactile communication. In one example, the patient asks a question, which is addressed via the automatic interaction. In a further example, the patient makes a statement which is reacted to via the automatic interaction with an adjustment of a parameter of the magnetic resonance examination.

The automatic interaction comprises, in at least one embodiment, at least providing an output as a function of a communication of the patient. An output can represent, for example, acoustic, visual and/or tactile communication. It is likewise conceivable, however, that the output comprises a transfer of an analog and/or digital signal, such as, for example, a control command and/or control signal. A communication preferably represents a content of the acoustic utterance of the patient. The communication can comprise, for example, an intention or a concern of the patient. It is conceivable, in particular, that the communication represents a reason for the patient communicating.

The output can represent, for example, a response to a question of the patient associated with the communication and be directed to the patient. It is likewise conceivable, however, that the output is directed to a user of the magnetic resonance apparatus and/or to a control unit of the magnetic resonance apparatus. In a preferred embodiment, the communication represents a concern or an intention of the patient, which is transmitted via the acoustic utterance of the patient. The acoustic utterance can comprise any desired acoustic signal, such as a sound, a word, a plurality of words, a sentence and/or a plurality of sentences. Preferably, the acoustic utterance of the patient comprises a deliberate communication of the patient. The acoustic utterance of the patient can also comprise an involuntary communication of the patient, however, such as a moan and/or a breathing noise.

The speech input unit is preferably configured, in at least one embodiment, to detect the acoustic utterance of the patient. The speech input unit can have a sound converter for this purpose, such as, for example, a sound sensor and/or a microphone, which transforms the acoustic utterance of the patient into an electrical signal. The speech input unit can have further components, such as an analog-to-digital converter, which digitizes the electrical signal and/or converts it into a machine-readable form. The acoustic utterance of the patient can thus be processed via a computing unit, in particular the speech processing unit.

The acoustic utterance of the patient, in at least one embodiment, is transferred to a speech processing unit for processing of the acoustic utterance of the patient. The speech processing unit preferably has a computing unit, which is configured to process the acoustic utterance. The computing unit is designed, in particular, to determine the communication of the patient, which is transferred via the acoustic utterance of the patient to the speech input unit. It is conceivable that the acoustic utterance is processed according to a pipeline model and/or via a semantic network, for example a neural network, a multi-layer, neural network (deep learning), in particular a MultiNet (multilayered extended semantic networks). For example, the speech processing can have one or more of the following step(s):

speech recognition,
tokenization,
morphological analysis,
syntactic analysis,
semantic analysis and
dialogue analysis.

It is conceivable that one or more of the implemented step(s) of the speech processing is carried out via use of an intelligent algorithm, such as, for example, a neural network or a multi-layer neural network, a statistical model and/or a logical model. Preferably, a significance is allocated to the acoustic utterance of the patient by determining the communication, and this can be used for an automatic interaction with the patient.

Furthermore, processing of the acoustic utterance of the patient, in at least one embodiment, comprises checking the communication for a correlation with a parameter of the magnetic resonance examination. A parameter of the magnetic resonance examination can comprise, for example, a property, a set of parameters, a group of parameters, a measuring process, a function, a program and/or an application of the magnetic resonance apparatus. It is conceivable, in particular, that a parameter of the magnetic resonance examination comprises an imaging sequence, a section of an imaging sequence and/or an imaging parameter of the imaging sequence. Parameters of the magnetic resonance examination thereby have, in particular, an effect on a property, a function and/or a progression of the magnetic resonance examination. For example, a head scan, a shoulder scan, a knee scan or the like may be set via the parameter "program". It is likewise conceivable that a group of parameters and/or measuring processes may be dynamically adapted via the parameter. For example, the measuring process can be adapted from a high resolution to a high speed since the patient remarks that they cannot lie down for much longer.

Preferably, a connection between the patient's concern transmitted with the acoustic utterance and a parameter is determined by checking the communication for a correlation with a parameter of the magnetic resonance examination. It is conceivable that a search, a classification and/or a categorization is used to identify the patient's concern and to infer a correct or incorrect assignment to a parameter of the magnetic resonance examination. If a correct assignment of the communication of the patient and one or more parameter(s) of the magnetic resonance examination are inferred, this assignment can be classified as the correct result. The classification can take place, for example, based upon an explanation and/or a description of parameters, which are stored in a database and can be provided as a space for a contextual search. Analogously, parameters with an incorrect context can be excluded from the search results and/or be classified as incorrect. For example a semantic search and/or a keyword search in a set of parameters of the magnetic resonance examination can be carried out as a function of the communication of the patient. Preferably, methods for annotation, in particular methods of text mining, are used in the case of the semantic search.

The output, in at least one embodiment, is determined as a function of the communication of the patient and of the parameter of the magnetic resonance examination. Preferably, the output comprises information about a parameter, which is correlated with the communication of the patient. The output can have, for example, information about a parameter range in which the parameter of the magnetic resonance examination can be changed. It is likewise conceivable that the output contains information about an automatic adjustment of the parameter of the magnetic resonance examination. Furthermore, the output can comprise a control signal, which can be used for actuation of a component of the magnetic resonance examination and/or a system in an examination room of the magnetic resonance apparatus. A component of the magnetic resonance apparatus can comprise, for example, a patient table, lighting, a public address system, or the like. A system in the examination room can comprise, for example, a lighting system, a public address system and/or an air-conditioning system. A parameter assigned to the communication can accordingly comprise a lighting intensity of the lighting system, a volume of the public address system and/or a speed of a fan of the air-conditioning system.

The output, in at least one embodiment, is provided via an output unit. Preferably, the output is provided via a suitable output unit. An output unit can be, for example a monitor, a screen, a projector, a loudspeaker, headphones, a display, a vibration system and the like. The output can take place by way of one or more output unit(s). For example, the patient and the user can be provided with the output by way of at least one loudspeaker and at least one display simultaneously or in a staggered manner. It is also conceivable that the output unit comprises a control interface. Control commands can be output from the output unit to components of the magnetic resonance apparatus and/or systems in the examination room via the control interface.

Automatic interaction with the patient can be provided by at least one embodiment of the inventive method. Questions and/or concerns of the patient can thus be attended to automatically so the user of the magnetic resonance apparatus is advantageously unburdened. Furthermore, interruptions to an activity of the user by the patient may be reduced or avoided, so user errors can be advantageously avoided. A further advantage results from the automatic checking of the communication for a correlation with a parameter of the magnetic resonance examination. A connection between the patient's concern and a parameter of the magnetic resonance examination can be reproducibly identified in a time-efficient manner hereby. Parameters can also be identified, which are not known to the user of the magnetic resonance apparatus and/or whose identification would be associated with an excessive time expenditure for the user.

In one embodiment of the inventive method, checking the communication for a correlation with a parameter of the magnetic resonance examination comprises a classification of the communication, wherein a parameter of the magnetic resonance examination is assigned to the communication via the classification.

The classification of the communication comprises, in at least one embodiment, at least one step from the group comprising: speech recognition, tokenization, morphological analysis, syntactic analysis, semantic analysis and dialogue analysis. It is conceivable that a neural network, a multi-layer network and/or a method of text mining is used to classify the communication with regard to a parameter of the magnetic resonance examination. Furthermore, use of logical and/or statistical models is conceivable. Preferably, at least one parameter of the magnetic resonance examination is assigned to the communication via the classification. This can mean that a parameter, which is assigned to a communication, has a connection with the patient's concern. It is likewise conceivable that a plurality of parameters is assigned to the communication via the classification.

In one embodiment, exactly one parameter is assigned to the communication via the classification. The one, assigned parameter can be connected with further parameters, however, which can likewise be assigned to the communication and/or the one parameter. The communication and a parameter can be assigned, for example, via formation of vectors, matrices, tuples and/or a data structure. In one example, the patient signals via the communication that a body region, which is situated in an imaging region of the magnetic resonance examination, is heating up undesirably. The classification of the communication can produce a connection with the parameter of the specific absorption rate and assign the communication of the patient to the specific absorption rate. The specific absorption rate can in turn be connected with further parameters of the magnetic resonance examination, which are likewise assigned to the communication of the patient.

A time-efficient and robust assignment of the patient's concern to a relevant parameter of the magnetic resonance examination may be advantageously provided by the classification of the communication of the patient via one of the above-mentioned methods for speech processing.

According to a further embodiment of the inventive method, the communication is assigned via the classification to a time requirement of an imaging sequence of the magnetic resonance examination, wherein
  determining the output comprises determining information about a remaining duration of the magnetic resonance examination as a function of the time requirement of the imaging sequence and wherein
  providing the output comprises an output of the information about the remaining duration of the magnetic resonance examination to the patient.

In one example, via the acoustic utterance, the patient asks a question in respect of the remaining duration of the magnetic resonance examination. The acoustic utterance of the patient is received by the speech input unit, converted into an electrical signal and transferred to the speech processing unit. The speech processing unit can carry out one of the above-described methods to assign the concern, in the form of the communication, associated with the acoustic utterance to a parameter of the magnetic resonance examination. In one example, the communication of the patient can comprise the words "long", "duration", "wait" or the like, and this is assigned via the classification to the time requirement of an imaging sequence of the magnetic resonance examination. An imaging sequence can comprise, for example, a predetermined, sequence over time of excitation pulses and readout intervals.

The imaging sequence, in at least one embodiment, is determined by imaging parameters, which can likewise represent parameters of the magnetic resonance examination. The time requirement of the magnetic resonance examination can result for example from a sum of individual durations of excitation pulses and readout intervals. It is likewise conceivable, however, that the time requirement represents a known parameter of the imaging sequence, which can be assigned directly to the communication of the patient. In addition, general questions of the patient, such as, e.g. "How long have I been in the device already?", "What time is it?" and other simple questions are also conceivable. An automatic response to these questions can contribute to subjectively reducing the examination time for the patient and to reassuring or distracting the patient during the magnetic resonance examination.

The information about the remaining duration of the magnetic resonance examination can be determined, for example, based upon a difference between the time requirement of the imaging sequence and a time that has already elapsed since the beginning of the magnetic resonance examination. It is likewise conceivable, however, that the determination of the information about the remaining duration of the magnetic resonance examination comprises, for example, a determination of a graphics output, such as a clock, a progress bar and the like. The information about the remaining duration of the magnetic resonance examination can accordingly be output via a loudspeaker and/or a display.

The patient can be advantageously reassured by an automatic response to a question of the patient. As a result, attempts by the patient to make themselves noticeable and/or an urge to move by nervous patients can be reduced or avoided. Image artifacts, which can result due to movement of the patient during the magnetic resonance examination, may thus be advantageously reduced or avoided.

In a further embodiment of the inventive method, the communication is assigned via the classification to a workflow of the imaging sequence of the magnetic resonance examination, wherein determining the output comprises determining information about a possible instant of an interruption of the magnetic resonance examination as a function of the workflow of the imaging sequence and wherein providing the output comprises an output of the information about the possible instant of interruption of the magnetic resonance examination to the patient and/or a user of the magnetic resonance apparatus.

It is conceivable that the communication of the patient indicates discomfort and/or a desire to terminate the magnetic resonance examination. In this case, the communication of the patient can be assigned to a workflow of the imaging sequence, which has, for example, a number and a duration of excitation pulses and/or readout intervals. It is likewise conceivable that the magnetic resonance examination has a plurality of imaging sequences, which are temporally aligned.

The information about a possible instant of an interruption can be determined as a function of the workflow of the imaging sequence and/or a remaining duration of an imaging sequence of the plurality of imaging sequences. Preferably, the possible instant of the interruption is determined as a function of the workflow of the imaging sequence in such a way that at least one current readout interval and/or a current imaging sequence can be excluded before the magnetic resonance examination is interrupted. It is likewise conceivable that an urgency of the patient's concern is taken into account.

In one embodiment, information about use of a contrast medium, which is incorporated by the parameter of the progression of the magnetic resonance examination, is assigned to the communication of the patient. The corresponding parameter can thus be taken into account when determining the possible instant of the interruption. It is conceivable for example that the information about the possible instant of interruption of the magnetic resonance examination includes a question as to whether the implementation of at least one further readout interval or the next imaging sequence is reasonable for the patient owing to a degradation over time of the contrast medium. The information about the possible instant of interruption of the magnetic resonance examination can also comprise a time specification in respect of an intended interruption of the magnetic resonance examination, however. The output can preferably be made to the patient, but also to the user of the magnetic resonance examination.

A suitable instant for the interruption of the magnetic resonance examination may advantageously be identified as a function of individual boundary conditions of the magnetic resonance examination, such as administration of a contrast medium, by taking into account the parameters of the magnetic resonance examination assigned to the communication of the patient.

In a further embodiment of the inventive method, the communication is assigned via the classification to a breathing compensation of the imaging sequence of the magnetic resonance examination, wherein determining the output comprises determining information about a possible adjustment of a breathing interval of the magnetic resonance examination as a function of the breathing compensation of the magnetic resonance examination and wherein providing the output comprises an output of the information about the possible adjustment of the breathing interval of the magnetic resonance examination to the patient and/or the user.

It is conceivable that the communication of the patient indicates a problem in respect of a breathing instruction of the magnetic resonance examination. The breathing instruction can comprise, in particular, a breathing stoppage or a breathing interval, which is transmitted to the patient as an instruction in order to minimize movement artifacts. The communication of the patient can be assigned in this case to the breathing compensation of the imaging sequence. The breathing compensation can have, for example, a number and a duration of excitation pulses, readout intervals as well as breaks and/or can be connected thereto. It is conceivable that a parameter of the breathing compensation is adjusted such that an excitation of nuclear spins and/or a readout of magnetic resonance signals is avoided during a breathing movement of the patient.

Determining the output, in at least one embodiment, comprises determining information about a possible adjustment of the breathing instruction as a function of the breathing compensation of the magnetic resonance examination. For this purpose, an analysis can be carried out as to the extent a parameter of the breathing compensation, such as, for example, the duration of excitation pulses, readout intervals and breaks, can be adjusted to better coordinate the breathing instruction with the patient's concern. In one example, the communication of the patient indicates that the duration of the current breathing interval is too long. Parameter variations can be established as a function of the assignment of the communication of the patient to the duration of excitation pulses and/or of readout intervals, which variations are better coordinated with a requirement of the patient. Information about a possible adjustment of the breathing interval may then be determined, and this is output via the output unit. The output can be made, for example, to the user of the magnetic resonance apparatus. The user can take note of and/or confirm the information about the adjustment of the breathing interval. In particular, the information about the adjustment can also be output to the patient, however, who is informed about the change to the breathing interval.

The user can be advantageously unburdened by the automatic determination of the information about the possible adjustment of the breathing interval as a function of the communication of the patient. Furthermore, the information about the adjustment of the breathing compensation can advantageously occur as a function of a large number of imaging parameters, which is unmanageable for the user and/or cannot be considered by the user for the duration of the magnetic resonance examination.

According to one embodiment of the inventive method, a correlation of the communication with at least one parameter of the magnetic resonance examination is established during checking of the communication for a correlation with a parameter of the magnetic resonance examination, also having the following step:

automatically adjusting the at least one parameter of the magnetic resonance examination as a function of the communication of the patient.

The communication can be checked for a correlation with a parameter of the magnetic resonance examination in accordance with one of the above-described embodiments. Preferably, parameters, which are connected with the patient's concern, are assigned to the communication of the patient. The speech processing unit can be connected to a computing unit and/or a control unit of the magnetic resonance apparatus in order to enable automatic adjustment of at least one parameter of the magnetic resonance examination as a function of the communication of the patient. It is conceivable that during adjustment of the at least one parameter, a parameter is adjusted, which is assigned to the communication of the patient. It is likewise conceivable, however, that further parameters, which are connected with the assigned parameter, are adjusted.

In one example, the communication of the patient relates to an interruption of the magnetic resonance examination. For this purpose, a duration of an excitation pulse and/or a readout interval, which are assigned to the communication of the patient, can be adjusted such that the magnetic resonance examination can be interrupted. In a further example, the communication of the patient relates to a shortening of the breathing interval of the magnetic resonance examination. Here a duration of an excitation pulse and/or a duration of a readout interval can be adjusted to adjust the breathing interval to an individual requirement of the patient. In a further example, the communication of the patient relates to a low temperature in the examination room of the magnetic resonance examination. For example a temperature control of an air-conditioning system can be assigned to the communication via the classification. It is conceivable that the temperature control of the air-conditioning system is automatically adjusted as a function of the communication of the patient. Apart from the described parameters, an assignment and/or adjustment of any other and/or further parameters of the magnetic resonance examination is of course conceivable.

In one embodiment, the output is used directly to output a control command for automatic adjustment of the at least one parameter to a component of the magnetic resonance apparatus and/or a system in the examination room of the magnetic resonance apparatus. For example, the determined information about the adjustment of a breathing interval of the magnetic resonance examination can simultaneously comprise a control command with which the breathing compensation of the magnetic resonance examination is adjusted.

Advantageously, a control command for adjustment of a parameter of the magnetic resonance examination may be provided with the classification of the parameter as a function of the communication and determining of the output. A time-efficient reaction to the patient's concern may thus be advantageously ensured.

In a further embodiment of the inventive method,
determining the output comprises determining a request to make an acoustic utterance again in respect of the at least one parameter of the magnetic resonance examination, wherein
providing the output comprises an output of the request to make the acoustic utterance again in respect of the communication to the patient.

It is conceivable that the communication of the patient can be determined only partially, for example owing to interfering noise, an unclear enunciation and/or an unclear sentence structure of the patient. This can mean that while a keyword is identified, which can be assigned to a parameter of the magnetic resonance examination, determination of a specific concern of the patient is not possible. It is likewise conceivable that at least one parameter of the magnetic resonance examination was changed as a function of the communication of the patient and checking of the patient's concern is expedient. For this purpose, an output can be provided, which asks the patient to make an utterance again in respect of the communication. When determining the request to make the acoustic utterance again, a parameter is preferably indicated, which was identified when determining the communication. It is likewise conceivable that the patient is advised via the output of a specific adjustment of the at least one parameter. The patient can be asked, in particular, to make an acoustic utterance again with regard to the communication in order to establish whether the patient is content with the adjustment of the at least one parameter.

The patient can advantageously react to an adjustment of the at least one parameter of the magnetic resonance examination by way of the request of the patient to make an acoustic utterance again in respect of the one parameter of the magnetic resonance examination. Furthermore, the patient can be asked to make an acoustic utterance again if the determination of the communication of the patient based upon the acoustic utterance is incorrect. Problems with speech recognition of the patient may thus advantageously be solved without intervention by the user being necessary.

In one embodiment of the inventive method, an incompatibility is established when checking the communication for a correlation with a parameter of the magnetic resonance examination, wherein
determining the output comprises determining information about the incompatibility and wherein
providing the output comprises an output of the information about the incompatibility to the user of the magnetic resonance apparatus and/or to the patient.

Establishing an incompatibility can mean that an assignment of a parameter of the magnetic resonance examination to the communication of the patient is inconclusive. It is likewise conceivable that the patient's concern associated with the acoustic utterance requires an adjustment of at least one parameter, which lies outside of a parameter range permitted for the imaging sequence. In such and other cases it can be expedient to determine information about the incompatibility and to provide the patient and/or the user of the magnetic resonance apparatus with this information. The information about the incompatibility can comprise, in particular, technical information about a permitted change to at least one parameter of the magnetic resonance examination and/or a proposal for an alternative imaging sequence. Such information is preferably output to the user of the magnetic resonance apparatus. It is likewise conceivable that the information about the incompatibility comprises an indication that a member of medical staff is dealing with the patient's concern. Such information is preferably output to the patient. In a preferred embodiment, the patient and the user can be provided with output units corresponding to different items of information.

The user can be advantageously advised of a discrepancy between the patient's concern and the current imaging sequence by the provision of the information about the incompatibility. Furthermore, the user can be provided with information about alternative imaging sequences, which are compatible with the patient's concern. As a result, a magnetic resonance examination may advantageously be provided, which contributes to a calm magnetic resonance examination of the patient.

In a further embodiment of the inventive method, determining the output comprises determining a disclosure about
- a previously detected acoustic utterance of the patient and/or
- a previously provided output to the patient wherein providing the output comprises an output of the disclosure to the user of the magnetic resonance apparatus.

It is conceivable that the detected acoustic utterance of the patient is output approximately in real time to the user of the magnetic resonance apparatus. This can be the case in particular if at least a most recent acoustic utterance of the patient includes a keyword, which indicates a high priority and/or urgency of the communication of the patient. It is likewise conceivable, however, that detected acoustic utterances of the patient are output to the user as collective recordings if a patient's concern cannot be resolved by the automatic interaction. Here, in particular, an exchanged dialogue can also be output, which comprises the outputs with which the patient has previously been provided and the detected acoustic utterances of the patient. It is also conceivable that determining the output comprises determining a disclosure about a previously undertaken adjustment of a parameter of the magnetic resonance examination. Previously undertaken adjustments of parameters of the magnetic resonance examination can thus be output to the user.

The user can be advantageously informed about a progression of a previous automatic interaction with the patient by the output of previously detected acoustic utterances of the patient, previously provided outputs to the patient and/or previously undertaken adjustments of a parameter of the magnetic resonance examination. As a result, the user can be advantageously provided with a basis for a decision, using which it is possible for the user to promptly intervene when an acute problem occurs during the magnetic resonance examination.

According to a further embodiment of the inventive method, determining the communication as a function of the acoustic utterance is inconclusive, wherein determining the output comprises
- determining a request to make an acoustic utterance again and/or
- determining information about an inconclusive determination of the communication and wherein providing the output comprises an output
- of the request to make the acoustic utterance again and/or
- of the information about the inconclusive determination of the communication to the patient and/or the user of the magnetic resonance apparatus.

Determining the communication of the patient can be inconclusive for example if processing the communication via the speech processing unit fails, does not deliver a meaningful result and/or delivers at least one keyword whose context cannot be determined. In such cases, determining the output can comprise determining a request to repeat and/or reword the acoustic utterance and/or the patient making an acoustic utterance again. By providing such an output the patient is asked to make an acoustic utterance again based upon which a communication can be determined. It is likewise conceivable, however, that information about the inconclusive determination of the communication is determined when determining the output. Such information can include, for example, at least some of the acoustic utterance of the patient, at least part of a particular communication and/or at least one keyword, which is determined as a function of the acoustic utterance. The user of the magnetic resonance apparatus is preferably provided with such information via the output. The output can comprise a speech output, such as the part of the acoustic utterance, and a visual output, such as presentation of the keyword on a display or a comparable visual output unit.

The patient and/or the user may be advised of the inconclusive determination of the communication by the output of information about the inconclusive determination of the communication and/or the request to repeat the acoustic utterance. It is conceivable that communication may be determined based upon the acoustic utterance of the patient after the repetition and/or rewording. The automatic interaction with the patient can be advantageously continued in this case without interrupting the activity of the user. Furthermore, after a predetermined number of inconclusive repetitions of the acoustic communication of the patient, the user can be advantageously informed about the existence of a problem when determining the communication of the patient.

In one embodiment of the inventive method, determining the communication also comprises determining a priority level of the communication, wherein the priority level is evaluated at least as a function of a limit value and wherein
- determining the output comprises determining information about the priority level of the communication and wherein
- providing the output comprises an output of the communication to the user of the magnetic resonance apparatus, if the priority level exceeds a first limit value.

A priority level of the communication can comprise, for example, a measure of the urgency of the communication of the patient, a measure of a potential danger to the patient and/or a measure of the urgency of an adjustment of a parameter of the magnetic resonance examination in view of a remaining duration of the magnetic resonance examination. Preferably, the priority level is determined at least as a function of the communication of the patient. It is likewise conceivable, however, that at least one parameter of the magnetic resonance examination, such as, for example, a remaining duration of the imaging sequence and/or a specific absorption rate, is taken into account when determining the priority level. The priority level is evaluated as a function of a limit value. Preferably, the priority level is evaluated as a function of a plurality of limit values. It is conceivable that a predetermined action and/or a predetermined output take place when the priority level exceeds a limit value.

In one example, a first limit value relates to a state of anxiety of the patient, which is determined based upon the communication of the patient and quantified via the priority level. It is conceivable that the user is informed when the first limit value is exceeded. For this purpose, information about the priority level of the communication can be determined and provided to the user via an output unit. Determining the information can comprise, in particular, determining a visual output, which advises the user via a warning signal of a required interaction with the patient.

A required interaction of the user with the patient can be advantageously automatically quantified by the determination of the priority level of the communication. The user of the magnetic resonance apparatus can thus pursue an activity undisturbed until information about exceeding of the first limit value is output to the user.

In a further embodiment of the inventive method, the magnetic resonance examination is interrupted if the priority level exceeds a second limit value, with the second limit value being greater than the first limit value.

The second limit value can indicate, for example, an immediate danger to the patient. In one example, as a function of the communication of the patient an undesirable side effect of a contrast medium and/or an undesirably high specific absorption rate can be inferred, which results in too high a ranking of the priority level. When an acute danger to the patient is established, preferably a warning signal is determined when determining the information about the priority level of the communication, which signal, together with the information, is output to the user of the magnetic resonance apparatus. Determining the information can also comprise a determination of courses of action, which counteract the danger to the patient. It is conceivable, in particular, that when determining the information about the priority level, a control command is determined, which interrupts the magnetic resonance examination. The warning signal can be output, for example, via a loudspeaker as an acoustic signal, for example an alarm, and a display. Preferably, the user is advised via the information of a cause of the high priority level and/or possible courses of action. Providing the output can also comprise an output of a control command for the interruption of the magnetic resonance examination.

Advantageously, the user can be advised of a potential danger to the patient and/or possible courses of action by the output of information about the priority level. As a result, faulty actions by the user can be advantageously avoided. Furthermore, it is possible for the user to intervene promptly so the risk of danger to the patient can be advantageously reduced.

At least one embodiment is directed to a magnetic resonance apparatus comprising a computing unit, a speech input unit, a speech processing unit and an output unit, wherein the computing unit is designed to coordinate a method of at least one embodiment of the invention and carry it out via the magnetic resonance apparatus.

The speech input unit is preferably designed to detect an acoustic utterance of the patient, such as, for example, a speech communication and/or a sound, and forward it to the speech processing unit. The speech input unit can have, in particular, a microphone and/or a sound sensor for this purpose. The speech processing unit is preferably configured to determine a communication as a function of the acoustic utterance of the patient. In particular, for the classification of the communication with regard to a parameter of the magnetic resonance examination, the speech processing unit can have a data exchange with the computing unit of the magnetic resonance apparatus and/or be integrated in it. An output unit is preferably configured to output acoustic, visual and/or tactile information, such as, for example, a vibration, to a user of the magnetic resonance apparatus or a patient.

For acquisition, processing and storage of data, such as, e.g. magnetic resonance data, magnetic resonance images, electrical signals of acoustic utterances, machine-readable data and/or data in machine-readable file formats and the like, apart from the computing unit, the magnetic resonance apparatus can have a control unit, a working memory, a data storage unit and a suitable interface for the input and output of data. The computing unit can comprise, for example, a controller, a microcontroller, a CPU, a GPU or the like. The working memory and the data storage units can have storage technologies such as RAM, ROM, PROM, EPROM, EEPROM, flash memory, but also HDD storage devices, SSD storage devices or the like. It is conceivable that the data storage unit represents an internal database, which is electrically and/or mechanically connected to the computing unit of the magnetic resonance apparatus. It is likewise conceivable, however, that the data storage unit is an external database, which is connected via a network connection to the computing unit. Examples of external storage units are network servers with corresponding data storage units and Cloud storage devices. The data can be transferred via analog and/or digital signals and suitable electrical and/or wireless signal connections between the components of the magnetic resonance apparatus.

The computing unit and/or the speech processing unit are preferably electrically connected to a control unit of the magnetic resonance apparatus and/or integrated in the control unit. The control unit can be configured to carry out an inventive method coordinated by the computing unit. The control unit can be configured, for example, to carry out a magnetic resonance measurement of the examination object, acquire magnetic resonance data of the examination object and transfer the magnetic resonance data to other components, such as the computing unit and/or the storage unit. It is likewise conceivable that the control unit is designed to adjust parameters of the magnetic resonance apparatus and/or further systems as a function of a control command of the computing unit and/or the speech processing unit. The computing unit can be configured to read the magnetic resonance data and create magnetic resonance images based upon the magnetic resonance data. Furthermore, the computing unit can be configured to carry out a classification of the communication of the patient and assign parameters of the magnetic resonance examination to the communication. Preferably, the computing unit is likewise configured to determine and/or undertake an adjustment of a parameter of the magnetic resonance examination as a function of the communication. In a further example, the computing unit is configured to determine information about a parameter, which can be output via the output unit to the patient and/or the user of the magnetic resonance apparatus. Furthermore, the computing unit and/or the speech processing unit can be designed to determine a communication of the patient, assign the communication to a parameter of the magnetic resonance examination and/or transfer information as a function of the parameter and/or communication to the output unit.

The speech input unit, the speech processing unit, the computing unit and the output unit of the inventive magnetic resonance apparatus can be advantageously coordinated with each other, enabling a time-efficient and robust implementation of an inventive method. In particular, the inventive magnetic resonance apparatus can be designed to coordinate and carry out a progression of individual method steps largely autonomously. It is conceivable that no expert knowledge is required for an interpretation of a provided output of an inventive method, so the output can be advantageously interpreted by any member of medical staff and/or the patient.

At least one embodiment of the invention is directed to a computer program product which can be loaded into a data storage unit of a computing unit of the magnetic resonance apparatus and which has program code segments to carry out at least one embodiment of an inventive method when the computer program product is run in the computing unit of the magnetic resonance apparatus.

The computing unit can be a computing unit of the magnetic resonance apparatus and/or a computing unit of a speech processing unit. At least one embodiment of the inventive method can be carried out quickly, in an identically repeatable manner and robustly by way of at least one embodiment of the inventive computer program product. The computer program product is configured such that it can carry out at least one embodiment of the inventive method steps via the computing unit. The computing unit must in each case have the requirements, such as an appropriate working memory, an appropriate graphics card or an appropriate logic unit, so the respective method steps can be efficiently carried out.

In at least one embodiment, the computer program product is stored, for example, on a computer-readable medium or on a network, a server or a Cloud, from where it can be loaded into the processor of a local computing unit. The computing unit can be designed as a stand-alone system component or as part of the magnetic resonance apparatus. Furthermore, control information of the computer program product can be stored on an electronically readable data carrier. The control information of the electronically readable data carrier can be configured in such a way that it carries out at least one embodiment of an inventive method when the data carrier is used in the computing unit of the magnetic resonance apparatus. Examples of electronically readable data carriers are a DVD, a magnetic tape, a USB stick or any other data storage unit on which electronically readable control information, in particular software, is stored. When this control information is read from the data carrier and transferred to a control unit and/or the computing unit of the magnetic resonance apparatus, all inventive embodiments of the described, inventive method can be carried out.

FIG. 1 illustrates one possible embodiment of the inventive magnetic resonance apparatus 10. The magnetic resonance apparatus 10 comprises a magnetic unit 11, which has, for example, a permanent magnet, an electromagnet or a superconducting main magnet 12 for generation of a strong and, in particular, homogeneous main magnetic field 13. In addition, the magnetic resonance apparatus 10 comprises a patient receiving region 14 for receiving a patient 15. In the present example embodiment the patient receiving region 14 is cylindrical and surrounded in a circumferential direction by the magnetic unit 11. Basically, designs of the patient receiving region 14 different from this example are also conceivable, however.

The patient 15 can be positioned in the patient receiving region 14 via a patient support apparatus 16 of the magnetic resonance apparatus 10. The patient support apparatus 16 has for this purpose a patient table 17 configured to move inside the patient receiving region 14. The magnetic unit 11 also has a gradient coil 18 for generating magnetic gradient fields, which is used for a spatial encoding during imaging. The gradient coil 18 is actuated via a gradient control unit 19 of the magnetic resonance apparatus 10. The magnetic unit 11 can also comprise a radio frequency antenna, which in the present example embodiment is designed as a body coil 20 permanently integrated in the magnetic resonance apparatus 10. The body coil 20 is configured for excitation of nuclear spins, which are situated in the main magnetic field 13 generated by the main magnet 12. The body coil 20 is actuated by a radio frequency unit 21 of the magnetic resonance apparatus 10 and irradiates radio frequency excitation pulses into an image acquisition region, which is formed substantially by a patient receiving region 14 of the magnetic resonance apparatus 10. The body coil 20 is also designed to receive magnetic resonance signals.

The magnetic resonance apparatus 10 has a control unit 22 for control of the main magnet 12, the gradient control unit 19 and for control of the radio frequency unit 21. The control unit 22 is designed to control implementation of a sequence, such as an imaging GRE (gradient echo) sequence, a TSE (turbo spin echo) sequence or an UTE (ultra-short echo time) sequence. In addition, the control unit 22 comprises a computing unit 28 for evaluation of magnetic resonance data, which is acquired during a magnetic resonance examination. The computing unit 28 of the magnetic resonance apparatus 10 can be designed to use reconstruction methods in order to reconstruct magnetic resonance images based upon the magnetic resonance data.

Furthermore, the magnetic resonance apparatus 10 comprises a user interface 23, which has a signal link to the control unit 22. Control information, such as, e.g. imaging parameters, but also reconstructed magnetic resonance images, can be displayed for a user on a display unit 24, for example on at least one monitor, of the user interface 23. Furthermore, the user interface 23 has an input unit 25, via which parameters of a magnetic resonance examination can be input by the user.

The computing unit 28 and/or the speech processing unit 32 can be designed to receive an acoustic utterance 44 of the patient 15 from a speech input unit 31 and process it. The computing unit 28 can have a speech processing unit 32 or be connected to a speech processing unit 32. The computing unit 28 and/or the speech processing unit 32 can also be designed to provide the patient 15 and/or a user of the magnetic resonance apparatus 10 with a result of the speech processing as an output 43 (see FIG. 2) via an output unit 33a. In the present example, detection of the acoustic utterance 44 of the patient 15 and provision of the output 43 take place via a combined speech input/output unit 31, 33a. The combined speech input/output unit 31, 33a can have, for example, a microphone and/or a sound sensor and a loudspeaker and/or a display in order to receive the acoustic utterance 44 of the patient 15 and provide the patient 15 with the output 43. In the illustrated example, the magnetic resonance apparatus 10 also has a second output unit 33b, which provides the user with an acoustic output 43. It is likewise conceivable, however, that a result of the speech processing is regularly displayed for the user on the user interface 23, such as, e.g. a screen with a loudspeaker.

In the present example, the computing unit 28 and/or the speech processing unit 32 are connected to a storage unit 29 of the magnetic resonance apparatus 10 and to a Cloud storage device 30. The computing unit 28 can be configured to store data such as, e.g. magnetic resonance images and/or magnetic resonance data on the storage unit 29 and/or the Cloud storage device 30 and to retrieve this data from the storage unit and/or the Cloud storage device via a suitable interface. It is conceivable in particular that the storage unit 29 and/or the Cloud storage device 30 have a database with explanations and/or descriptions of parameters of a magnetic resonance examination. The computing unit 28 and/or the speech processing unit 32 can be accordingly designed to access the database during the course of checking the communication of the patient 15 for a correlation with a parameter of the magnetic resonance examination. For example, the explanations and/or descriptions of the parameters can be used for a semantic search, a keyword search and/or a method of text mining. It is likewise conceivable that the communication of the patient 15 is classified via a Cloud computer (not shown), which has access to a search machine and the world wide web.

The magnetic resonance apparatus 10 can also have a local receiving antenna 26, which is positioned on a body region of the patient 15 and detects magnetic resonance signals of the body region of the patient 15 and transfers them to the computing unit 28 of the control unit 22. The local receiving antenna 26 preferably has an electrical connecting cable 27, which provides a signal link to the radio frequency unit 21 and the control unit 22. Like the body coil 20, the local receiving antenna 26 can also be designed for excitation of nuclear spins and for receiving magnetic resonance signals. The local receiving antenna 26 can be actuated by the radio frequency unit 21 for this purpose. In one example the local receiving antenna 26 is designed as a head coil, which at least partially surrounds the head of the patient 15. It is conceivable that the speech input unit 31 and/or the output unit 33 are integrated in the local receiving antenna 26.

The illustrated magnetic resonance apparatus 10 can of course comprise further components, which magnetic resonance apparatuses conventionally have. It is likewise conceivable that the magnetic resonance apparatus 10 has a C-shaped, a triangular or an asymmetric construction of the magnetic field-generating components instead of the cylindrical construction. The magnetic resonance apparatus 10 can in particular be designed to carry out a magnetic resonance examination of a standing or seated patient 15.

FIG. 2 shows a schematic arrangement of the speech input unit 31, the speech processing unit 32 and the output unit 33 of the inventive magnetic resonance apparatus 10. As shown in FIG. 1, the speech input unit 31 and the output unit 33 are preferably designed as combined speech input/output units 31a, 33a. A separate implementation of the speech input unit 31 and the output unit 33 is also conceivable, however. The combined speech input/output unit 31a, 33a is designed to receive an acoustic utterance 44 of the patient 15 via a microphone and provide the patient 15 with an output 43 via a loudspeaker. The combined speech input/output unit 31a, 33a is connected by a suitable signal line 46, such as, e.g. an electrical line or an optical fiber, to the computing unit 28 and/or the speech processing unit 32. Preferably, the combined speech input/output unit 31b, 33b is positioned for the user of the magnetic resonance apparatus 10 in a control room 41, which is used for control and/or monitoring of the magnetic resonance apparatus 10. In a preferred embodiment, the user is provided with an output 43 if the automatic interaction with the patient 15 is inconclusive and/or if the concern of the patient 15 cannot be addressed by an adjustment of a parameter of the magnetic resonance examination. In the illustrated example, the combined speech input/output unit 31b, 33b in the control room 41 has a speech input unit 34, which enables direct communication of the user with the patient 15. The combined speech input/output unit 31b, 33b and the combined speech input/output unit 31a, 33a can act like an intercom system for this purpose, with the computing unit 28 and/or the speech processing unit 32 coordinating, for example, a transmission of involved signals.

For automatic interaction with the patient 15 the speech processing unit 32 is designed to determine a communication of the patient 15 as a function of the acoustic utterance 44. The speech processing unit 32 can implement different methods of computer linguistics for this purpose, such as a pipeline model, but also a neural network, a multi-layer, neural network, a MultiNet and/or further methods. The speech processing unit 32 and/or the computing unit 28 are also designed, moreover, to assign the communication of the patient 15 to a parameter of the magnetic resonance examination. The processes can be accompanied or supported by a classification, a categorization, a keyword search, a semantic search and further methods. A change to a parameter of the magnetic resonance examination determined as a function of the communication of the patient 15 can be implemented on the magnetic resonance apparatus 10, for example automatically, via the computing unit 28 or the control unit 22.

FIG. 3 shows an example flowchart of processing of an acoustic utterance 44 of the patient 15 according to one embodiment of an inventive method. Individual processing steps of the method can take place in an order different to that described here. In particular, individual processing steps of those described here can be omitted and/or be replaced by alternative methods and/or methods of computer linguistics. In the run-up to speech processing, the acoustic utterance 44 detected via the speech input unit 31a is transmitted to the speech processing unit 32 as an electrical signal. The electrical signal is preferably an analog or a digital signal, which can be subsequently transformed by the speech processing unit 32 into a preferred signal and/or file format.

Speech recognition takes place in a processing step LS1. Speech recognition can comprise a conversion of the electrical signal into machine-readable data. Machine-readable data is characterized in particular in that it can be processed by a computer, in particular the computing unit 28 and/or the speech processing unit 32. Machine-readable data can be in the form, inter alia, of binary code, hexadecimal numbers, a high-level language and/or in the form of suitable file formats, such as RDFa, HTML, CSV, XML and the like. The acoustic utterance 44 of the patient 15 is preferably converted into a text form, which is suitable for processing in subsequent processing steps.

The tokenization takes place in a processing step LS2, in which the acoustic utterance 44 are segmented into words, sentence components and/or sentences.

According to a further processing step LS3, a morphological analysis of the words, sentence components and/or sentences is carried out. In particular the grammar, such as a conjugation and/or a case, is analyzed in order to attribute individual words to their basic forms. In particular, a subsequent classification and/or a semantic search may be carried out and/or simplified based upon the determined basic forms.

In a processing step LS4, a syntactic analysis is carried out. Different structural functions, such as subject, predicate, object, adverbial, attribute and the like, are assigned to words in a sentence here. Knowledge of the syntactic function of words can simplify further processing steps, such as the assignment of the concern of the patient 15 when determining the communication during the course of a semantic analysis. In addition, syntactic functions, such as a statement, a question and/or a command, can be assigned to sentence components and/or whole sentences.

In a further processing step LS5, the semantic analysis of words, sentence components and sentences is carried out. The semantic analysis comprises, in particular, an examination of a frequency of what are known as content words as well as their content-related function and their expressive value (for example denotation, connotation, figurative meaning, coherence). The semantic analysis can have large number of individual steps. In particular, the semantic analysis of individual words, individual sentences or a plurality of connected sentences can take place via the use of neural networks, multi-layer neural networks (for example MultiNet) and/or different methods of text mining or be supported by them.

According to a processing step LS6, a dialogue analysis is carried out in which relationships between successive sentences are determined. A dialogue analysis can be used not just when determining the communication of the patient 15, but, in particular, also with automatic interaction with the patient 15, such as a response to a question or posing of a question.

Preferably, functions of the speech processing unit 32, which can be necessary for the above-mentioned processing steps LS1 to LS6, are also used in the creation and output of speech communication to the patient 15 and/or the user of the magnetic resonance apparatus 10. The relevant functions can be used not just for the determination of the communication as a function of the acoustic utterance 44 of the patient 15, but also for checking the communication for a correlation with a parameter of the magnetic resonance examination.

FIG. 4 shows a flowchart of an embodiment of an inventive method for automatic interaction with a patient 15 during a magnetic resonance examination, wherein the automatic interaction comprises at least providing an output as a function of a communication of the patient 15.

In a step S1, an acoustic utterance 44 of the patient 15 is detected via a speech input unit 31. In one example, the acoustic utterance 44 of the patient 15 is detected via a microphone, which is integrated in the speech input unit 31a of the magnetic resonance apparatus 10. The acoustic utterance 44 of the patient 15 is transformed on detection into an electrical signal, which can be transferred to the speech processing unit 32. It is conceivable that the speech input unit 31 has a computing unit, which filters a detected electrical signal, so an acoustic utterance 44 of the patient 15 can be distinguished from background noise and/or interfering noise. In this way, only acoustic utterances 44 of the patient 15 are transferred to the speech processing unit 32. In this embodiment, the processing step LS1 takes place in the speech input unit 31a already. Appropriate filtering can also be carried out in the speech processing unit 32, however.

In a step S2, the acoustic utterance 44 of the patient 15 is processed via a speech processing unit 32, with the processing of the acoustic utterance 44 comprising at least determining of the communication as a function of the acoustic utterance 44 and checking the communication for a correlation with a parameter of the magnetic resonance examination. Preferably, processing the acoustic utterance 44 of the patient 15 comprises at least one of the steps described in FIG. 3 to determine the communication of the patient 15. It is conceivable in particular that a multi-layer, neural network is used to determine the communication of the patient as a function of the acoustic utterance 44. It is likewise conceivable, however, that keywords are determined based upon the acoustic utterance 44, which can be used for a determination of the communication and/or checking the communication for a correlation with a parameter of the magnetic resonance examination.

In one embodiment, checking the communication for a correlation with a parameter of the magnetic resonance examination comprises a classification of the communication, with a parameter of the magnetic resonance examination being assigned to the communication via the classification. Preferably, a neural network, a multi-layer network and/or a method of text mining is used to classify the communication with regard to a parameter of the magnetic resonance examination. The classification can comprise a formation of tuples and/or matrices, which assign one or more parameter(s) of the magnetic resonance examination to the communication of the patient.

In a further embodiment, an incompatibility is established when checking the communication for a correlation with a parameter of the magnetic resonance examination since the assignment of a parameter of the magnetic resonance examination to the communication of the patient is inconclusive.

In one embodiment, determining the communication also comprises determination of a priority level of the communication, with the priority level being evaluated at least as a function of a limit value. A priority level may be assigned to the communication as a function of the communication of the patient 15 and/or keywords of the communication. Communications which indicate a danger to the patient 15 are allocated, for example, a higher priority level than communications, which imply discomfort of the patient 15. Preferably, the priority levels of the communication are evaluated with limit values to which different tasks, recommended courses of action and/or instructions for action are allocated. For example, when a first limit value is exceeded the user can be automatically notified, while the magnetic resonance examination is interrupted immediately when a second limit value is exceeded.

In a step S3, at least one parameter of the magnetic resonance examination is automatically adjusted as a function of the communication of the patient 15. The speech processing unit 32 can transfer the communication of the patient 15 and a parameter, which is associated with the concern of the patient 15, to the computing unit 28 in order to adjust a parameter of the magnetic resonance examination. The computing unit 28 can determine an adjustment of the parameter, for example as a function of the concern of the patient 15 transferred with the communication, the associated parameter and the current imaging sequence. Preferably, the computing unit 28 transfers a control command for adjustment of the parameter to the control unit 22, which automatically implements the adjustment of the parameter during the magnetic resonance examination.

According to a step S4, the output is determined as a function of the communication of the patient and of the parameter of the magnetic resonance examination. For example, different tasks can be determined as a function of the communication of the patient 15, an assigned parameter and a priority level of the communication. In particular, determining the output can comprise one or more of the following step(s): determining information about a remaining duration of the magnetic resonance examination as a function of a time requirement of an imaging sequence, information about a possible instant of an interruption of the magnetic resonance examination as a function of a workflow of the imaging sequence, information about a possible adjustment of a breathing interval of the magnetic resonance examination as a function of a breathing compensation of the magnetic resonance examination, a request to make an acoustic utterance again 44 in respect of the at least one parameter of the magnetic resonance examination, information about the incompatibility, a disclosure about a previously undertaken adjustment of a parameter of the magnetic resonance examination a request to make an acoustic utterance again 44, information about an inconclusive determination of the communication and/or information about the priority level of the communication.

Preferably, a format is defined as early as when determining the output 43, which format enables suitable provision of the output 43. This format can depend on various factors, such as, e.g. the concern of the patient 15, the parameter of the magnetic resonance examination, the information and/or the priority level of the communication. In one example a warning signal, which indicates an acute danger to the patient 15, is preferably output via an alarm signal via a loudspeaker, while the output 43 of the information about the incompatibility can expediently take place on a display and/or monitor of the user interface 23.

In a step S5, the output 43 is provided via an output unit 33. In particular, one or more of the task(s) 43 determined in step S4 can be provided in the process. Apart from the above-mentioned factors, the format of the output 43 can also depend on a target of the output 43. The target of the output 43 can be, for example, the patient 15, the user, the control unit 22 of the magnetic resonance apparatus 10 and/or a system in the examination room 40. If the target of the output 43 is a person, preferably an acoustic, a visual and/or a tactile output 43 is used, which speaks to a sensory perception of the person. If, by contrast, the output 43 is directed to the control unit 22 of the magnetic resonance apparatus 10, a component of the magnetic resonance apparatus 10 and/or a system in the examination room 40, preferably a signal, in particular a control signal, is used. Information, a request, a disclosure and/or a control signal can be transferred, for example, via an analog and/or digital signal. The information and/or the control signal can be transferred to the output unit 33 in a wired manner or wirelessly.

Of course, the embodiments of the inventive method and the inventive magnetic resonance apparatus described here should be understood as being example. Individual embodiments can be expanded by features of other embodiments, therefore. In particular, the order of the method steps of the inventive method should be understood as being example. The individual steps can also be carried out in a different order or can partially or completely overlap time-wise.

The patent claims of the application are formulation proposals without prejudice for obtaining more extensive patent protection. The applicant reserves the right to claim even further combinations of features previously disclosed only in the description and/or drawings.

References back that are used in dependent claims indicate the further embodiment of the subject matter of the main claim by way of the features of the respective dependent claim; they should not be understood as dispensing with obtaining independent protection of the subject matter for the combinations of features in the referred-back dependent claims. Furthermore, with regard to interpreting the claims, where a feature is concretized in more specific detail in a subordinate claim, it should be assumed that such a restriction is not present in the respective preceding claims.

Since the subject matter of the dependent claims in relation to the prior art on the priority date may form separate and independent inventions, the applicant reserves the right to make them the subject matter of independent claims or divisional declarations. They may furthermore also contain independent inventions which have a configuration that is independent of the subject matters of the preceding dependent claims.

None of the elements recited in the claims are intended to be a means-plus-function element within the meaning of 35 U.S.C. § 112(f) unless an element is expressly recited using the phrase "means for" or, in the case of a method claim, using the phrases "operation for" or "step for."

Example embodiments being thus described, it will be obvious that the same may be varied in many ways. Such variations are not to be regarded as a departure from the spirit and scope of the present invention, and all such modifications as would be obvious to one skilled in the art are intended to be included within the scope of the following claims.

What is claimed is:

1. A method for automatic interaction with a patient during a magnetic resonance examination with a magnetic resonance apparatus, the method comprising:
   detecting an acoustic utterance of the patient;
   processing the acoustic utterance of the patient, via a speech processor, by
      determining a communication of the patient as a function of the acoustic utterance, and
      checking the communication for a correlation with a parameter of the magnetic resonance examination, the checking the communication including
         classifying the communication by assigning the parameter of the magnetic resonance examination to the communication, and
         assigning the communication, via the classification to a time requirement of an imaging sequence of the magnetic resonance examination;
   determining an output as
      a function of the communication of the patient and the parameter of the magnetic resonance examination, and
      information about a remaining duration of the magnetic resonance examination as a function of a time requirement of an imaging sequence; and providing the output to the patient.

2. The method of claim 1, further comprising:
   assigning, the communication, via the classification, to a workflow of the imaging sequence of the magnetic resonance examination, wherein
   the determining of the output includes
      determining information about a possible instant of an interruption of the magnetic resonance examination as a function of the workflow of the imaging sequence, and
   the providing the output includes outputting the information about the possible instant of interruption of the magnetic resonance examination to at least one of the patient or a user of the magnetic resonance apparatus.

3. The method of claim 1, further comprising:
   assigning the communication, via the classification, to a breathing compensation of the imaging sequence of the magnetic resonance examination, wherein
   the determining the output includes
      determining information about a possible adjustment of a breathing interval of the magnetic resonance examination as a function of the breathing compensation of the magnetic resonance examination, and
   the providing the output includes
      outputting the information about the possible adjustment of the breathing interval of the magnetic resonance examination to at least one of the patient or a user of the magnetic resonance apparatus.

4. The method of claim 1, further comprising:
   establishing a correlation of the communication with the parameter of the magnetic resonance examination; and
   automatically adjusting the parameter of the magnetic resonance examination as a function of the communication of the patient.

5. The method of claim 4, wherein the determining the output includes determining a disclosure about a previous adjustment of a parameter of the magnetic resonance examination, and
  wherein the providing the output includes outputting the disclosure to a user of the magnetic resonance apparatus.

6. The method of claim 1, wherein the determining the output includes determining a request to make a second acoustic utterance respect of the parameter of the magnetic resonance examination, and
  wherein the providing the output includes outputting the request to make the second acoustic utterance.

7. The method of claim 1, wherein the checking the communication includes establishing an incompatibility,
  wherein the determining the output includes determining information about the incompatibility, and
  wherein the providing the output includes outputting the information about the incompatibility to at least one of a user of the magnetic resonance apparatus or the patient.

8. The method of claim 1, wherein
  the determining the output includes determining a disclosure about at least one of
    a previously detected acoustic utterance of the patient, or
    a previously provided output to the patient, and
  wherein the providing the output includes outputting the disclosure to a user of the magnetic resonance apparatus.

9. The method as claimed in claim 1, wherein in response to the determining the communication as a function of the acoustic utterance being inconclusive, the determining the output includes at least one of
  determining a request to make a second acoustic utterance, or
  determining information about an inconclusive determination of the communication, and
  wherein the providing the output includes outputting of at least one of
    the request to make the second acoustic utterance, to at least one of the patient or a user of the magnetic resonance apparatus, or
    the information about the inconclusive determination of the communication to at least one of the patient or the user of the magnetic resonance apparatus.

10. The method of claim 1, wherein the determining the communication includes determining a priority level of the communication, the priority level being evaluated at least as a function of a limit value,
  wherein the determining the output includes determining information about the priority level of the communication, and
  wherein the providing the output includes outputting the communication to a user of the magnetic resonance apparatus in response to the information about the priority level indicating a priority level exceeding a first limit value.

11. The method of claim 10, further comprising:
  interrupting the magnetic resonance examination in response to the information about the priority level indicating a priority level exceeding a second limit value, the second limit value being greater than the first limit value.

12. A magnetic resonance apparatus, comprising:
  a speech input device;
  an output device; and
  processing circuitry configured to
    detect an acoustic utterance of a patient via the speech input device,
    process the acoustic utterance of the patient by,
      determining a communication of the patient as a function of the acoustic utterance, and
      checking the communication for a correlation with a parameter of a magnetic resonance examination, the checking the communication including
        classifying the communication by assigning the parameter of the magnetic resonance examination to the communication, and
        assigning the communication, via the classification, to a time requirement of an imaging sequence of the magnetic resonance examination,
    determine an output as
      a function of the communication of the patient and the parameter of the magnetic resonance examination, and
      information about a remaining duration of the magnetic resonance examination as a function of a time requirement of an imaging sequence, and provide the output to the patient via the output device.

13. A non-transitory computer readable storage medium, storing computer-readable instructions that, when executed by one or more processors, cause a magnetic resonance apparatus to:
  detect an acoustic utterance of a patient;
  process the acoustic utterance of the patient, via a speech processor, by
    determining a communication of the patient as a function of the acoustic utterance, and
    checking the communication for a correlation with a parameter of a magnetic resonance examination, the checking the communication including
      classifying the communication by assigning the parameter of the magnetic resonance examination to the communication, and
      assigning the communication, via the classification, to a time requirement of an imaging sequence of the magnetic resonance examination;
  determine an output as
    a function of the communication of the patient and the parameter of the magnetic resonance examination, and
    information about a remaining duration of the magnetic resonance examination as a function of a time requirement of an imaging sequence; and
  provide the output to the patient.

14. A method for automatic interaction with a patient during a magnetic resonance examination with a magnetic resonance apparatus, the method comprising:
  detecting an acoustic utterance of the patient;
  processing the acoustic utterance of the patient, via a speech processor, by
    determining a communication of the patient as a function of the acoustic utterance, and
    checking the communication for a correlation with a parameter of the magnetic resonance examination;
  establishing a correlation of the communication with the parameter of the magnetic resonance examination;

automatically adjusting the parameter of the magnetic resonance examination as a function of the communication of the patient;
determining an output as a function of the communication of the patient and the parameter of the magnetic resonance examination; and providing the output.

15. A method for automatic interaction with a patient during a magnetic resonance examination with a magnetic resonance apparatus, the method comprising:
detecting an acoustic utterance of the patient;
processing the acoustic utterance of the patient, via a speech processor, by
determining a communication of the patient as a function of the acoustic utterance, and
checking the communication for a correlation with a parameter of the magnetic resonance examination;
determining an output as (i) a function of the communication of the patient and the parameter of the magnetic resonance examination, and (ii) a request to make a second acoustic utterance, the determining the output including
determining the request to make the second acoustic utterance in respect of the parameter of the magnetic resonance examination; and providing the output.

16. A method for automatic interaction with a patient during a magnetic resonance examination with a magnetic resonance apparatus, the method comprising:
detecting an acoustic utterance of the patient;
processing the acoustic utterance of the patient, via a speech processor, by
determining a communication of the patient as a function of the acoustic utterance, and
checking the communication for a correlation with a parameter of the magnetic resonance examination by establishing an incompatibility;
determining information about the incompatibility;
determining an output as
a function of the communication of the patient and the parameter of the magnetic resonance examination, and
the information about the incompatibility; and
providing the output to at least one of a user of the magnetic resonance apparatus or the patient.

17. A method for automatic interaction with a patient during a magnetic resonance examination with a magnetic resonance apparatus, the method comprising:
detecting an acoustic utterance of the patient;
processing the acoustic utterance of the patient, via a speech processor, by
determining a communication of the patient as a function of the acoustic utterance, and
checking the communication for a correlation with a parameter of the magnetic resonance examination;
determining a disclosure about at least one of
a previously detected acoustic utterance of the patient, or
a previously provided output to the patient
determining an output as
a function of the communication of the patient and the parameter of the magnetic resonance examination, and
the disclosure; and
providing the output to a user of the magnetic resonance apparatus.

18. A method for automatic interaction with a patient during a magnetic resonance examination with a magnetic resonance apparatus, the method comprising:
detecting an acoustic utterance of the patient;
processing the acoustic utterance of the patient, via a speech processor, by
determining a communication of the patient as a function of the acoustic utterance by determining a priority level of the communication, the priority level being evaluated at least as a function of a limit value, and
checking the communication for a correlation with a parameter of the magnetic resonance examination;
determining information about the priority level of the communication;
determining an output as a function of the communication of the patient and the parameter of the magnetic resonance examination; and
providing the output to a user of the magnetic resonance apparatus in response to the information about the priority level indicating a priority level exceeding a first limit value.

19. A magnetic resonance apparatus, comprising:
a speech input device;
an output device; and
processing circuitry configured to
detect an acoustic utterance of a patient via the speech input device,
process the acoustic utterance of the patient by
determining a communication of the patient as a function of the acoustic utterance, and
checking the communication for a correlation with a parameter of a magnetic resonance examination,
establish a correlation of the communication with the parameter of the magnetic resonance examination,
automatically adjust the parameter of the magnetic resonance examination as a function of the communication of the patient,
determine an output as a function of the communication of the patient and the parameter of the magnetic resonance examination, and
provide the output via the output device.

20. A magnetic resonance apparatus, comprising:
a speech input device;
an output device; and
processing circuitry configured to
detect an acoustic utterance of a patient via the speech input device,
process the acoustic utterance of the patient by
determining a communication of the patient as a function of the acoustic utterance, and
checking the communication for a correlation with a parameter of a magnetic resonance examination,
determine an output as (i) a function of the communication of the patient and the parameter of the magnetic resonance examination, and (ii) a determined request to make a second acoustic utterance in respect of the parameter of the magnetic resonance examination, and
provide the output via the output device.

21. A magnetic resonance apparatus, comprising:
a speech input device;
an output device; and
processing circuitry configured to
    detect an acoustic utterance of a patient via the speech input device,
    process the acoustic utterance of the patient by
        determining a communication of the patient as a function of the acoustic utterance, and
        checking the communication for a correlation with a parameter of a magnetic resonance examination by establishing an incompatibility,
    determine information about the incompatibility,
    determine an output as
        a function of the communication of the patient and the parameter of the magnetic resonance examination, and
        the information about the incompatibility, and
    provide the output, via the output device, to at least one of a user of the magnetic resonance apparatus or the patient.

22. A magnetic resonance apparatus, comprising:
a speech input device;
an output device; and
processing circuitry configured to
    detect an acoustic utterance of a patient via the speech input device,
    process the acoustic utterance of the patient by
        determining a communication of the patient as a function of the acoustic utterance, and
        checking the communication for a correlation with a parameter of a magnetic resonance examination,
    determine a disclosure about at least one of
        a previously detected acoustic utterance of the patient, or
        a previously provided output to the patient,
    determine an output as
        a function of the communication of the patient and the parameter of the magnetic resonance examination, and
        the disclosure, and
    provide the output to a user of the magnetic resonance apparatus via the output device.

23. A magnetic resonance apparatus, comprising:
a speech input device;
an output device; and
processing circuitry configured to
    detect an acoustic utterance of a patient via the speech input device,
    process the acoustic utterance of a patient by
        determining a communication of the patient as a function of the acoustic utterance by determining a priority level of the communication, the priority level being evaluated at least as a function of a limit value, and
        checking the communication for a correlation with a parameter of a magnetic resonance examination,
    determine information about the priority level of the communication,
    determine an output as a function of the communication of the patient and the parameter of the magnetic resonance examination, and
    provide the output to a user of the magnetic resonance apparatus, via the output device, in response to the information about the priority level indicating a priority level exceeding a first limit value.

* * * * *